United States Patent
Netzhammer

(10) Patent No.: US 12,319,553 B2
(45) Date of Patent: Jun. 3, 2025

(54) DEVICE FOR HOISTING LOADS

(71) Applicant: Castus Sterile Systems GmbH & Co. KG, Ochsenhausen (DE)

(72) Inventor: Eric Netzhammer, Arlesheim (CH)

(73) Assignee: Castus Sterile Systems GmbH & Co. KG, Ochsenhausen (DE)

(*) Notice: Subject to any disclaimer, the term of this patent is extended or adjusted under 35 U.S.C. 154(b) by 269 days.

(21) Appl. No.: 17/913,962

(22) PCT Filed: Mar. 24, 2021

(86) PCT No.: PCT/EP2021/057613
§ 371 (c)(1),
(2) Date: Sep. 23, 2022

(87) PCT Pub. No.: WO2021/191300
PCT Pub. Date: Sep. 30, 2021

(65) Prior Publication Data
US 2023/0150806 A1    May 18, 2023

(30) Foreign Application Priority Data
Mar. 25, 2020 (CH) ..................... 00357/20

(51) Int. Cl.
*B66F 9/065* (2006.01)
*A61L 2/26* (2006.01)

(52) U.S. Cl.
CPC .............. *B66F 9/065* (2013.01); *A61L 2/26* (2013.01)

(58) Field of Classification Search
CPC .... B66F 9/065; B66F 3/00; B66F 5/00; B66F 7/00; B66F 7/06; B66F 7/0666; A61L 2/26
USPC ........................................... 254/2 R
See application file for complete search history.

(56) References Cited

U.S. PATENT DOCUMENTS

| | | | |
|---|---|---|---|
| 5,144,369 A * | 9/1992 | Benedict | G03G 15/0896 399/119 |
| 6,835,362 B1 * | 12/2004 | Eriksson | A61L 2/26 422/26 |
| 2004/0005259 A1 * | 1/2004 | Sacca | A61L 2/26 422/298 |
| 2015/0314026 A1 | 11/2015 | Mauzerall et al. | |

(Continued)

FOREIGN PATENT DOCUMENTS

| | | | | |
|---|---|---|---|---|
| CN | 109229179 A * | 1/2019 | | |
| EP | 2823828 A1 * | 1/2015 | | A61L 2/26 |

(Continued)

OTHER PUBLICATIONS

International Searching Authority, Search Report issued in PCT/EP2021/057613, mailed Jun. 18, 2021 (5 pages).

(Continued)

*Primary Examiner* — C. A. Rivera

(74) *Attorney, Agent, or Firm* — Wood Herron & Evans LLP

(57) ABSTRACT

A positioning system for horizontal and vertical positioning of loads located on a trolley is preferably used to dock containers filled with cleaned and sterilized small parts to a transfer device. For this purpose, a lifting device is arranged on the trolley for vertical movement of the container. A pull-in device causes the trolley to move horizontally to the position required for docking.

8 Claims, 4 Drawing Sheets

(56) References Cited

U.S. PATENT DOCUMENTS

2018/0154403 A1* 6/2018 Netzhammer ............ A61L 2/26
2019/0175774 A1 6/2019 Snyder et al.
2021/0276806 A1* 9/2021 Knepp ................. B62D 53/005

FOREIGN PATENT DOCUMENTS

| EP | 3253422 A1 | 12/2017 |
|---|---|---|
| WO | 0061199 A1 | 10/2000 |
| WO | 2017055201 A1 | 4/2017 |
| WO | 2017152327 A1 | 9/2017 |

OTHER PUBLICATIONS

Switzerland Patent Office, Search Report issued with initial publication of priority application CH717259A1, published Sep. 30, 2021 (search report from Jul. 16, 2020 on pp. 7-10 of publication).

* cited by examiner

DEVICE FOR HOISTING LOADS

CROSS-REFERENCE TO RELATED APPLICATIONS

This application is a national phase entry of, and claims priority to, International Application No. PCT/EP2021/057613, filed Mar. 24, 2021, which claimed priority to Swiss Patent Application No. CH 00357/20, filed on Mar. 25, 2020, the entire contents of which are herein incorporated by reference.

TECHNICAL FIELD

This application relates to a system for precise horizontal and vertical positioning of loads located on a trolley, preferably containers filled with cleaned and sterilized small parts, in order to dock them at a transfer device.

BACKGROUND

In the prior art, containers containing the small parts to be treated, i.e. to be cleaned and/or sterilized, or treated, are lifted off a transport trolley, a so-called trolley, by a stationary device for docking to a treatment station or a transfer device at a so-called isolator and brought into the position suitable for docking. Such positioning devices are described, for example, in the International PCT Application No. WO 00/74735 or in the European Patent Application No. EP 1 769 889.

In the International PCT Application No. WO 00/61199, a container is shown being removed from a treatment station after treatment on a trolley with a lifting device, which latter is obviously used to remove the container from the treatment station in the suitable vertical position.

From the European Patent Application No. EP 3 253 422, a cleaning device is known, which is characterized in that a container filled with small parts to be treated, which is stored on a transport trolley and firmly connected to it, is not lifted off the trolley for docking at a treatment station, but that it is docked remaining on the trolley and that it remains on the trolley during the entire treatment.

In the known solutions for positioning a container at a transfer device, it is disadvantageous that a stationary positioning device is required in addition to the trolley. Such devices, when mounted on the floor, require a lot of space and are usually disruptive. The devices, which are mounted on the ceiling, require large dimensioned brackets, since the forces due to long levers are extreme.

Thus, it would be desirable to precisely position a treatment container remaining on a transport trolley for docking with a transfer device.

SUMMARY

To address these and other problems with conventional devices and methods, a transport trolley, of the type defined above, is provided so as to include the features described below. To this end, the transport trolley includes a positioning system with a lifting device arranged on the trolley for vertical movement of a load, and with a pull-in device for horizontal movement of the trolley with the load.

BRIEF DESCRIPTION OF THE DRAWINGS

In the following, preferred embodiments of the invention are described with reference to the accompanying drawings. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

Figure 1A:
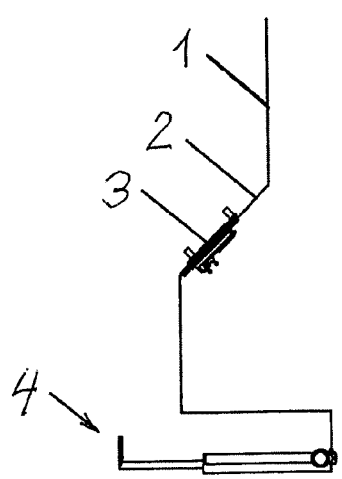
FIGS. 1a and 1b are side and perspective views of a transfer station where a container is to be docked, in accordance with embodiments of the invention.
Figure 1B:
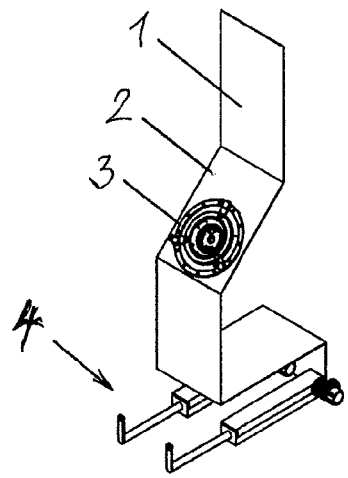

The FIGS. 1a to 4b each show a side view "a" and a perspective view "b." An isolator wall 1 shown in the FIGS. 1a and 1b has a surface 2, which is inclined, for example, at 45°, in which the alpha part 3 of a rapid transfer port known per se is located. Below the part of the isolator equipped with the rapid transfer port, a pull-in device 4 for a trolley, described in more detail below, is arranged.

Figure 2A:
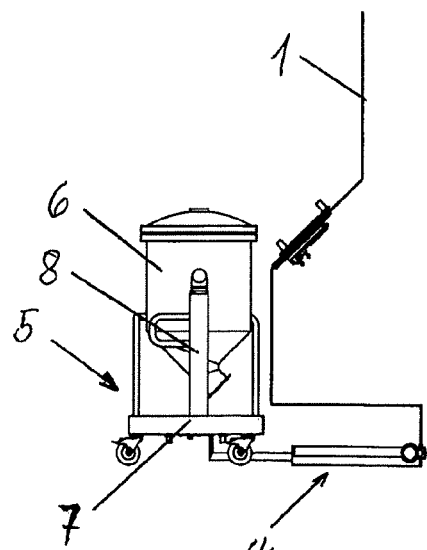
FIGS. 2a and 2b are side and perspective views of a trolley approaching the transfer station of FIGS. 1a and 1b, with a container stored thereon.
Figure 2B:
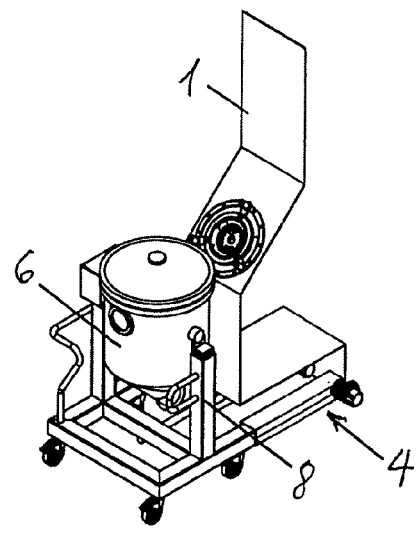

The FIGS. 2a and 2b similarly show a side view and a perspective view with a trolley 5 approaching the isolator, to which a treatment container 6 is fixedly connected. The trolley has a wheeled base 7 and two vertical telescopic lifting columns 8, at the upper ends of which are bearings for receiving corresponding bearing pins 9 attached to the container.

In a manner known per se, the lifting columns consist of several round or rectangular tubes arranged one inside the other, which are telescopically extended or retracted by a threaded spindle. The threaded spindle can be rotated manually or by an electric motor, preferably a servomotor. Depending on the clean room requirements, the telescopic extension and retraction of the lifting columns can also be driven hydraulically or pneumatically. Alternatively, the height adjustment can also be carried out by other drive elements known per se, such as chain drives, etc.

Figure 3A:
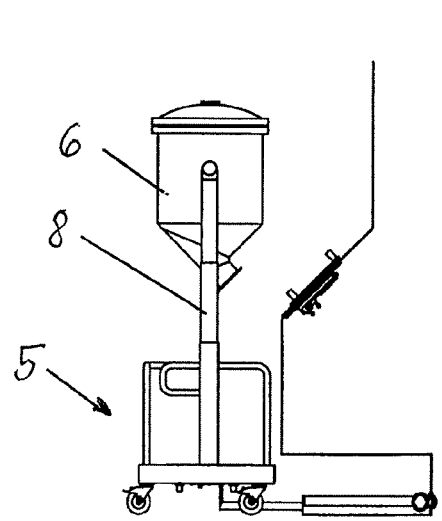
FIGS. 3a and 3b are side and perspective views of the container lifted on the trolley to the vertical position required for docking.
Figure 3B:
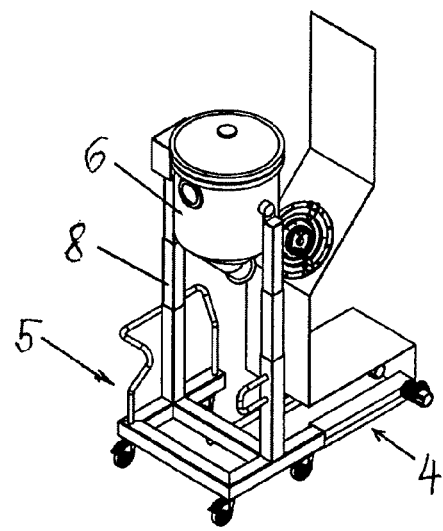

The FIGS. 3a and 3b show the container 6 lifted by the extended lifting columns 8, which is in the vertical position suitable for docking with the isolator.

The lifting columns of the trolley also allow the container to be lowered until its opening is at a height that allows the operator to load the container.

To allow docking, the trolley with the container still needs to be moved horizontally to the alpha part of the rapid transfer port. Instead of moving the container vertically and horizontally in succession, the container can also first be brought into a vertical position in which the axes of the alpha part and the beta part of the rapid transfer port located on the container are in line, and then, through a coordinated simultaneous movement of the lifting columns and the pull-in device, the two parts of the transfer port are brought coaxially to each other. For this purpose, the drive motors of the lifting columns and the pull-in device are controlled in a manner known per se by a control device.

Figure 4A:
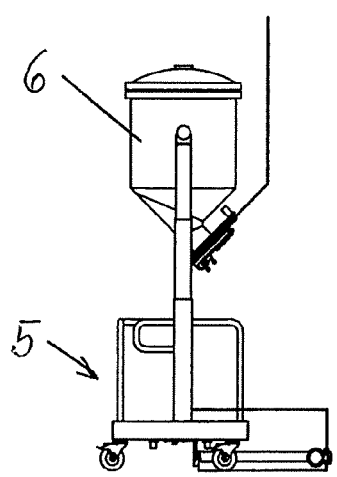
FIGS. 4a and 4b are side and perspective views of the container docked after horizontal retraction of the trolley.
Figure 4B:
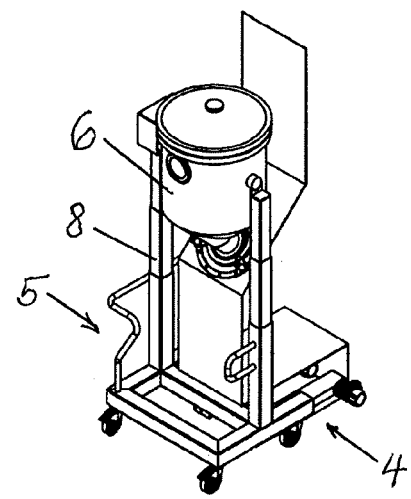

The FIGS. 4a and 4b show the container remaining on the trolley docked to the isolator for emptying.

A device for horizontal retraction of the trolley with the container consists of parts mounted on the floor and on the trolley. In the embodiment shown in the FIGS. 5a through 6b, this pull-in device consists of a device 4 mounted on the floor below the insulator, which, as shown in the FIG. 6a, consists of two spindle devices 10 arranged in parallel in housings with spindle rods 16 driven synchronously by motors 11, preferably servo or stepper motors, arranged inside traction tubes 12.

Figure 5A:
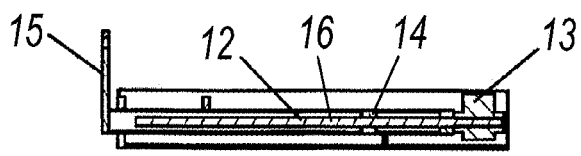
FIGS. 5a, 5b, and 5c are various detail views of parts of a device for horizontal retraction of the trolley.

The FIG. 5a shows a section through one of the spindle devices with a gear 13 for driving the spindle rods and spindle nuts 14 arranged inside the traction tubes and engaged with the spindle rods, which are moved horizontally by the spindle rods and thus extend or retract the traction tubes.

Figure 5B:
Figure 5C:
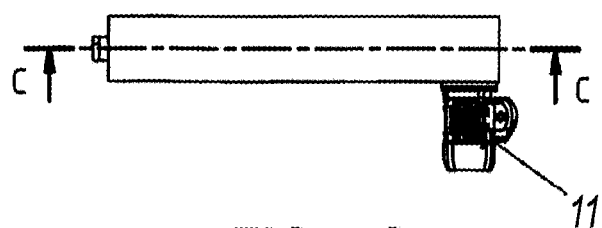

At the front of the traction tubes are latches 15 which, when extended, engage in suitable recesses (defining an engagement device 17) on the trolley. The FIG. 5b shows a side view of the spindle device 10. The FIG. 5c shows a top view in which the section according to the FIG. 5a is indicated by the line C-C.

Figure 7:
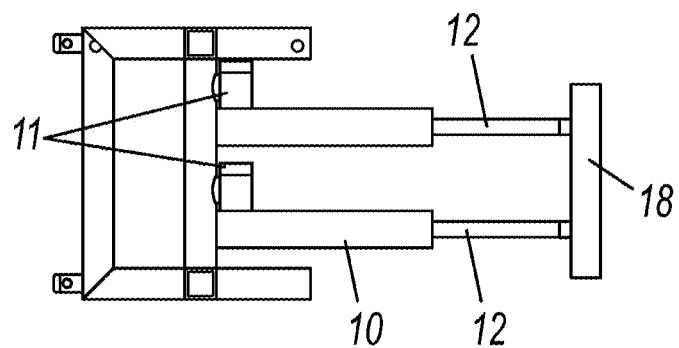
FIG. 7 is a top view of an alternative device for horizontal retraction of the trolley in which the drive causing the retraction is arranged on the trolley.

According to an alternative embodiment shown in FIG. 7, in which the floor remains largely free, the device for horizontal retraction of the trolley with the container is implemented in reverse form. The drive causing the retraction, i.e., for example, the spindle devices 10 and the latches 15, are not arranged on the floor but on the trolley, while on the floor there is only a simple fixed engagement device 18 in which the latches engage. For docking, the trolley is moved up to the engagement device. When the latches are in the docking position, they are engaged on the engagement device and fixed horizontally.

The container can now be lifted by the lifting device, and when the height is reached, the trolley can be moved towards the isolator by the spindle device.

Figure 6A:
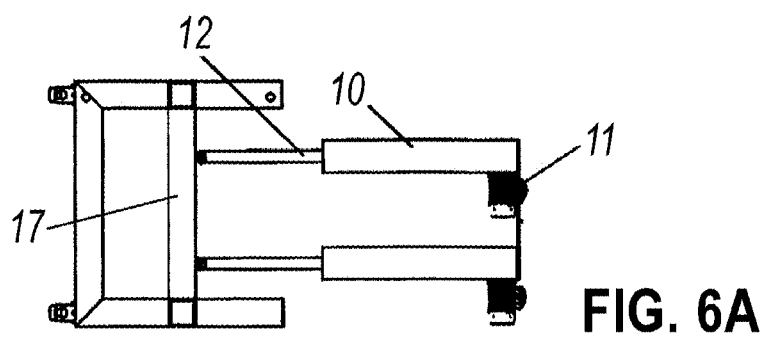
FIGS. 6a and 6b are top views of a device for horizontal retraction of the trolley without and with container and isolator.
Figure 6B:
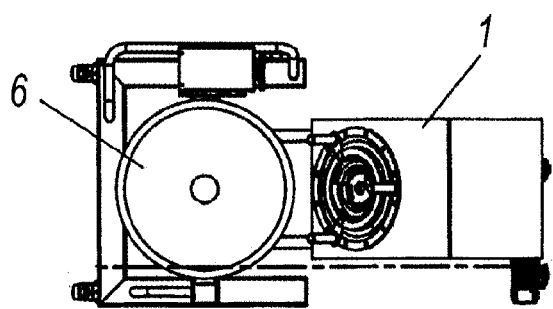

The FIG. 6b shows a top view of the trolley in the same position as in the FIG. 6a, but with the container 6 and the insulator 1.

What is claimed is:

1. A positioning system for horizontal and vertical positioning of a load on a trolley, in order to dock the load on a transfer device, comprising:
   the trolley;
   a rapid transfer port defining a portion of the transfer device;
   a lifting device arranged on the trolley for vertical movement of the load; and
   a pull-in device for horizontal movement of the trolley with the load,
   wherein the pull-in device is arranged underneath the rapid transfer port.

2. The positioning system of claim 1, wherein the load is a treatment container.

3. The positioning system of claim 2, wherein the treatment container is brought into a position suitable for docking with an isolator.

4. The positioning system of claim 1, wherein the pull-in device comprises motor-driven spindle devices provided with latches.

5. The positioning system of claim 4, wherein the spindle devices are arranged on a floor and that an engagement device is arranged on the trolley.

6. The positioning system of claim 4, wherein the spindle devices are arranged on the trolley and that an engagement device is arranged on a floor.

7. The positioning system of claim 2, wherein the lifting device is designed for lowering the container to a height suitable for loading the container.

8. The positioning system of claim 1, wherein the load includes containers configured to be filled with cleaned and sterilized parts.

* * * * *